(12) United States Patent
Thompson et al.

(10) Patent No.: US 10,434,242 B2
(45) Date of Patent: Oct. 8, 2019

(54) COVERS FOR DRUG CONTAINER PISTON ARRAYS OR PISTON NESTS AND PACKAGES FOR COVER AND PISTON NEST ASSEMBLIES

(71) Applicants: West Pharmaceutical Services, Inc., Exton, PA (US); Daikyo Seiko, Ltd., Sumida-ku (JP)

(72) Inventors: James Thompson, Reading, PA (US); Timothy Brommer, Morgantown, PA (US); Hideaki Kawamura, Sano (JP)

(73) Assignees: WEST PHARMACEUTICAL SERVICES, INC., Exton, PA (US); DAIKYO SEIKO, LTD., Tokyo (JP)

( * ) Notice: Subject to any disclaimer, the term of this patent is extended or adjusted under 35 U.S.C. 154(b) by 0 days.

(21) Appl. No.: 15/541,182

(22) PCT Filed: Jan. 9, 2015

(86) PCT No.: PCT/US2015/010826
§ 371 (c)(1),
(2) Date: Jun. 30, 2017

(87) PCT Pub. No.: WO2016/111698
PCT Pub. Date: Jul. 14, 2016

(65) Prior Publication Data
US 2017/0348476 A1    Dec. 7, 2017

(51) Int. Cl.
*A61M 5/00* (2006.01)
*B65D 71/70* (2006.01)
(Continued)

(52) U.S. Cl.
CPC ............ *A61M 5/001* (2013.01); *A61M 5/008* (2013.01); *B01L 3/5085* (2013.01);
(Continued)

(58) Field of Classification Search
USPC ........ 206/364, 518, 515, 519, 558; 220/513, 220/514, 507; 53/329, 397
See application file for complete search history.

(56) References Cited

U.S. PATENT DOCUMENTS 3,195,770 A * 7/1965 Robertson ............... B65D 1/36
                                                      206/486
3,469,686 A * 9/1969 Gutsche ............ H01L 21/67346
                                                      206/518
(Continued)

FOREIGN PATENT DOCUMENTS

CA      2877456 A1    1/2014
EP      1857794 A1    11/2007
(Continued)

OTHER PUBLICATIONS

Int'l Preliminary Report on Patentability dated Jul. 11, 2017 in Int'l Application No. PCT/US2015/010826.
(Continued)

*Primary Examiner* — Jacob K Ackun
(74) *Attorney, Agent, or Firm* — Panitch Schwarze Belisario & Nadel LLP (57) ABSTRACT

A cover for a drug container piston array includes a plurality of cover sections configured for positioning over the drug container piston array. Each cover section includes an elongated cover section body having an open base end and a closed capped end, and a plurality of base sections or a web positioned between the plurality of cover sections and coupled to each base end. Packaging assemblies including a cover and a piston nest are also disclosed.

14 Claims, 8 Drawing Sheets

(51) Int. Cl.
   *B65D 25/10*     (2006.01)
   *B01L 3/00*      (2006.01)
(52) U.S. Cl.
   CPC ........ *B01L 3/50853* (2013.01); *B65D 25/108*
          (2013.01); *B65D 71/70* (2013.01); *A61M*
          *2207/00* (2013.01); *B01L 2200/025* (2013.01);
          *B01L 2200/141* (2013.01); *B01L 2300/047*
          (2013.01); *B01L 2300/048* (2013.01); *B01L*
             *2300/069* (2013.01); *B01L 2300/0809*
          (2013.01); *B01L 2300/089* (2013.01); *B01L*
             *2300/123* (2013.01); *B01L 2400/0478*
                                                (2013.01)

(56)             References Cited

U.S. PATENT DOCUMENTS

| | | | | |
|---|---|---|---|---|
| 3,589,511 | A | | 6/1971 | Britt |
| 3,946,864 | A | * | 3/1976 | Hutson ................ B65D 71/70 |
| | | | | 206/725 |
| 3,982,655 | A | * | 9/1976 | Kaupert ................ B65D 1/36 |
| | | | | 220/23.6 |
| 4,838,417 | A | * | 6/1989 | Jeruzal ................ B65D 1/36 |
| | | | | 206/318 |
| 5,653,345 | A | * | 8/1997 | Knoss ................ B65D 11/188 |
| | | | | 206/470 |
| 5,826,712 | A | * | 10/1998 | Aikio ................ B65D 71/70 |
| | | | | 206/203 |
| 6,021,913 | A | * | 2/2000 | McGrath ................ B65D 71/70 |
| | | | | 206/427 |
| 6,193,088 | B1 | * | 2/2001 | Vincent ................ B01L 3/50825 |
| | | | | 215/248 |
| 6,702,139 | B2 | * | 3/2004 | Bergeron ................ B65D 1/36 |
| | | | | 206/521.1 |
| 8,047,373 | B2 | * | 11/2011 | Murphy ................ A47B 88/90 |
| | | | | 206/514 |
| 8,453,838 | B2 | * | 6/2013 | Hill ................ A61M 5/008 |
| | | | | 206/438 |
| 8,469,185 | B2 | * | 6/2013 | Nicoletti ............ B65D 77/0446 |
| | | | | 206/203 |
| 8,545,914 | B1 | * | 10/2013 | Mastroianni ............. B65D 1/36 |
| | | | | 206/508 |
| 8,800,800 | B2 | * | 8/2014 | Gerner ................ A61M 5/008 |
| | | | | 211/71.01 |
| 9,415,155 | B2 | * | 8/2016 | Togashi ................ A61M 5/008 |
| 2005/0011898 | A1 | * | 1/2005 | Van Handel ........... B65D 1/265 |
| | | | | 220/507 |
| 2006/0219594 | A1 | * | 10/2006 | Andrews ................ B65D 85/32 |
| | | | | 206/521.8 |
| 2009/0095647 | A1 | * | 4/2009 | Togashi ................ A61M 5/008 |
| | | | | 206/438 |
| 2009/0100802 | A1 | | 4/2009 | Bush et al. |
| 2011/0192756 | A1 | * | 8/2011 | Hill ................ A61M 5/008 |
| | | | | 206/515 |
| 2013/0186793 | A1 | * | 7/2013 | Gagnieux ............. A61M 5/002 |
| | | | | 206/364 |
| 2014/0353190 | A1 | * | 12/2014 | Okihara ................ A61M 5/002 |
| | | | | 206/370 |
| 2015/0000231 | A1 | * | 1/2015 | Ramirez ................ B65B 5/068 |
| | | | | 53/475 |
| 2015/0041349 | A1 | * | 2/2015 | Liversidge ............ A61M 5/008 |
| | | | | 206/364 |
| 2017/0348476 | A1 | * | 12/2017 | Thompson ........... B65D 25/108 |

FOREIGN PATENT DOCUMENTS

| | | |
|---|---|---|
| WO | 2010062602 A1 | 6/2010 |
| WO | 2011141549 A1 | 11/2011 |
| WO | 2012042291 A1 | 4/2012 |

OTHER PUBLICATIONS

Int'l Search Report & Written Opinion dated Sep. 1, 2015 in Int'l Application No. PCT/US2015/010826.

\* cited by examiner

COVERS FOR DRUG CONTAINER PISTON ARRAYS OR PISTON NESTS AND PACKAGES FOR COVER AND PISTON NEST ASSEMBLIES

CROSS-REFERENCE TO RELATED APPLICATION

This application is a section 371 of International Application No. PCT/US2015/010826, filed Jan. 9, 2015, which was published in the English language on Jul. 14, 2016 under International Publication No. WO 2016/111698, the disclosure of which is incorporated herein by reference.

BACKGROUND OF THE INVENTION

The present invention relates to covers for drug container piston or plunger arrays or piston nests, and packages for cover and piston nest assemblies.

For automated assembly purposes, individual drug containers pistons are often positioned in array form, i.e. rows and columns. As discussed herein, a piston array may include any number of pistons and is not limited to a particular matrix configuration. Preferably, the arrangement of a piston array is maintained during automated assembly by positioning individual drug container pistons in a piston nest.

A piston nest is typically a substantially planar tray that includes a plurality of individual nesting units. Each nesting unit is configured to receive a drug container piston. Exemplary piston nests are described in U.S. Pat. No. 8,453,838, which is incorporated herein by reference in its entirety.

During automated assembly of drug containers (e.g. syringes), a piston nest assembly, which includes the piston nest and a plurality pistons arranged in individual nesting units of the piston nest, is positioned above a similarly oriented tray with pre-filled drug container barrels. As assembly of the drug containers progresses, each piston from the piston nest is pressed into and aligned with an underlying drug container barrel, using automated means. Automated means may include, but is not limited to, mechanical pins and/or cams used to push each drug container piston out of a piston nest and into the underlying drug container barrel.

To assure that all assembled parts of the drug container are suitable for use, it is important to properly package the piston nest assembly, and orient individual pistons within the nesting unit for sterilization, as well as various stoppering and filling methods. When piston nest assemblies are properly packaged, various contaminants are prevented from negatively impacting sterilization, integrity and/or usability as a part of a primary container.

Current methods of packaging piston nest assemblies, however, do not include use of a cover or other structure that would protect and/or orient individual pistons for sterilization, stoppering, and filling of the drug container. Accordingly, there is a need for covers for drug container piston arrays and piston nests, as well as packages for cover and piston nest assemblies.

BRIEF SUMMARY OF THE INVENTION

In one preferred embodiment, a cover for a drug container piston array includes a plurality of cover sections configured for positioning over the drug container piston array. Each cover section includes a cover section body, having an open base end and a closed capped end, and a plurality of base sections positioned between the plurality of cover sections and coupled to each base end. Disposed within the cover section body are radially positioned locators placed in substantially equidistant intervals on inner surfaces of the cover section body.

In another preferred embodiment, a cover for a drug container piston array includes a plurality of transversely elongated cover sections. Each cover section includes an open base end and a closed capped end, and a cover web, extending around the plurality of cover sections and between the plurality of cover sections. The web is coupled to each base end such that the cover sections are interconnected.

Packages for a cover and piston nest assembly may include either embodiment of the cover and a piston nest disposed within a container.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements shown. In the drawings.

DETAILED DESCRIPTION OF THE INVENTION

Reference will now be made in detail to the present embodiments of the invention illustrated in the accompanying drawings. Wherever possible, the same or like reference numbers will be used throughout the drawings to refer to the same or like features. It should be noted that the drawings are in simplified form and are not drawn to a precise scale.

In reference to the disclosure herein, for purposes of convenience and clarity only, directional terms such as top, bottom, above, below, distal, and transverse, are used with respect to the accompanying drawings. Such directional terms used in conjunction with the following description of the drawings should not be construed to limit the scope of the invention in any manner not explicitly set forth herein. Unless specifically set forth herein, the terms "a", "an" and "the" are not limited to one element but instead should be read as meaning "at least one". The terminology includes the words noted above, derivatives thereof and words of similar import.

Turning in detail to the drawings, FIGS. 1-13 show various configurations of covers and embodiments of piston nest assemblies and packages for covers and piston nest assemblies. FIGS. 1-7 show a piston nest 10, a drug container piston array 12, and a cover 14, according to a first configuration, disposed within a container 16. Together these elements form a package 100 for a cover 14 and a piston nest assembly 20.

Figure 1:
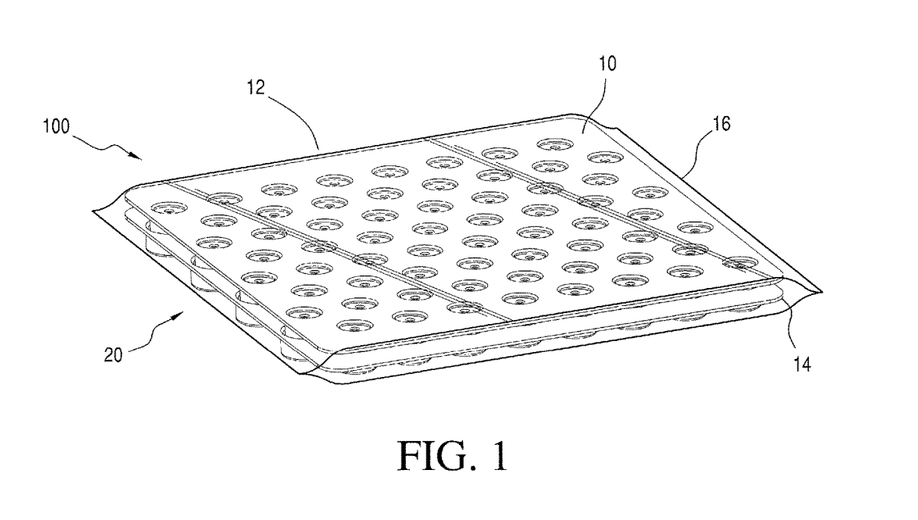
FIG. 1 is a perspective view of a package, including a first embodiment of a container and a cover and piston nest assembly in accordance with the present invention.
Figure 2:
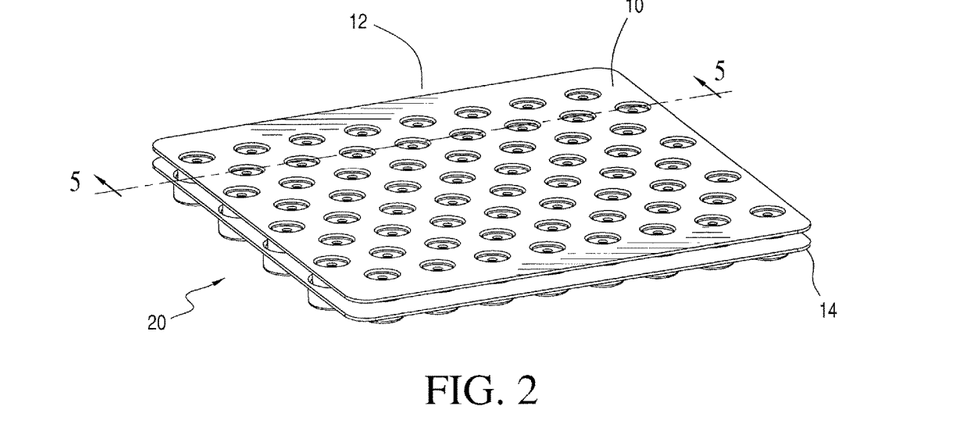
FIG. 2 is a perspective view of the cover and piston nest assembly included in the package of FIG. 1.
Figure 3:
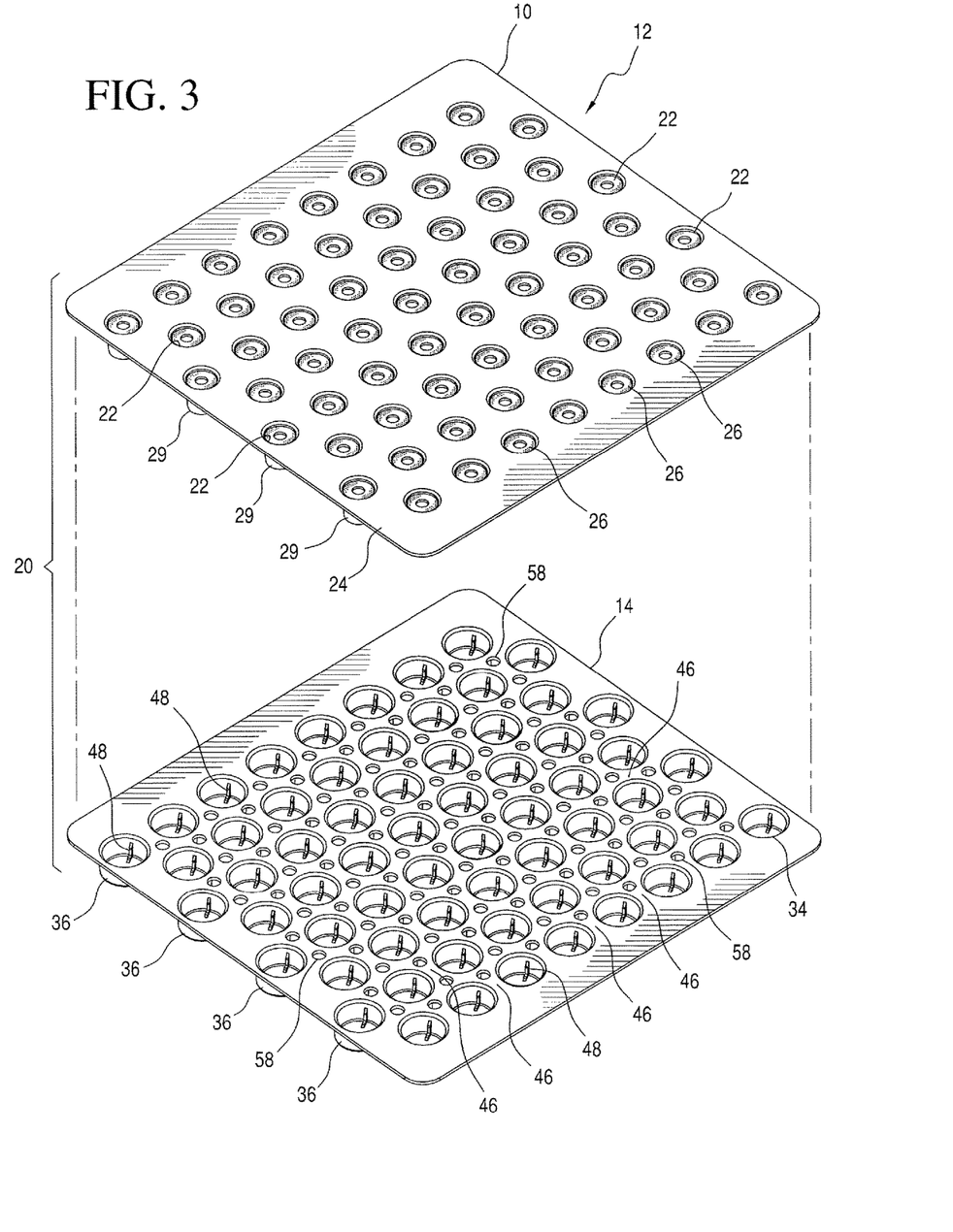
FIG. 3 is an enlarged exploded perspective view of the cover and piston nest assembly shown in FIG. 2.

The container 16 is preferably manufactured from one or more materials, which are suitable for sterilization and protection of a cover and a piston nest assembly 20 (FIGS. 2 and 9), particularly from contamination that could render a plurality of pistons 26 contained in the assembly unsuitable for subsequent use/assembly with a drug container. The container 16 may be any known container, which is suitable for housing sterilized pistons. Container types include STERIBAGS® sterile containers and other pre-sterilized containers known to those skilled in the art. FIGS. 2 and 3 show the cover 14 and the piston nest assembly 20 of FIG. 1, while FIGS. 9 and 10 show the cover 214 and the piston nest assembly 220 of FIG. 8.

Figure 10:
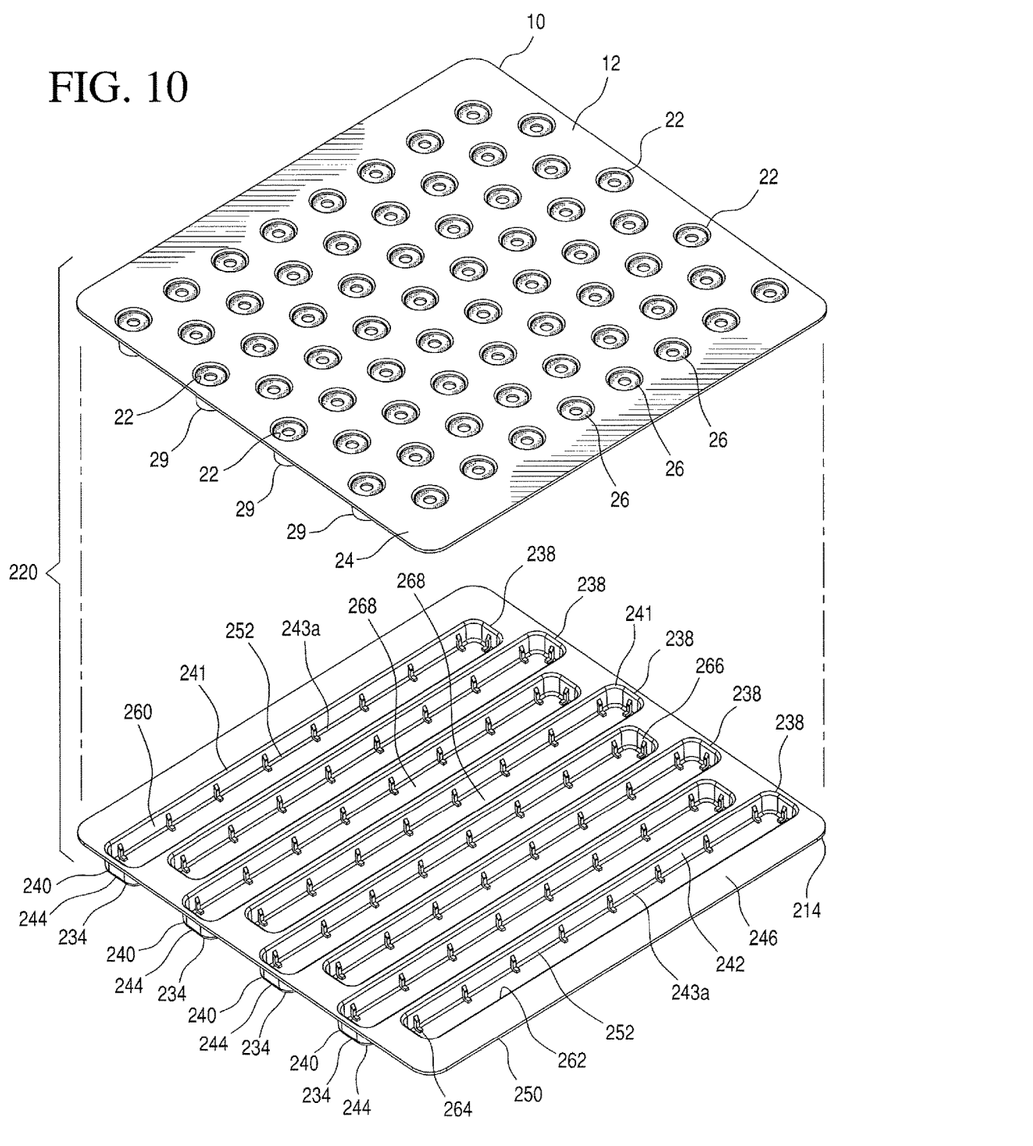
FIG. 10 is an enlarged exploded perspective view of the cover and piston nest assembly shown in FIG. 9.

Generally, a piston nest 10, as shown particularly in FIGS. 3 and 10, includes a plurality of spaced apart single nesting units 22, interconnected by a nest web 24. In a preferred configuration, the piston nest 10 can include one hundred spaced apart single nesting units 22. The piston nest 10, however, can be configured to include more or less than one hundred nesting units 22. The piston nest 10 can also include a piston 26 (FIG. 5) configured within each of the plurality of spaced apart single nesting units 22.

The piston nest 10 is generally configured as a planar tray with the single nesting units 22 connected in a planar fashion by the nest web 24. While the piston nest 10 is shown configured as a planar rectangular tray, the piston nest 10 can alternatively be configured into any planar fashion suitable for its intended use. For example, the outer perimeter 25 of the piston nest 10 may be configured as a square, a circle, an oval, an octagon, or various other shapes.

The piston nest 10 is preferably formed from one or more rigid materials such as rigid or semi-rigid polymeric materials, including, but not limited to, polyethylene, polycarbonate, polypropylene and/or composite combinations of materials. The chosen materials of construction preferably maintain the integrity of the pistons as well as not deform to a point of affecting machinability. Polypropylene, however, is preferred as the material for piston nests 10 because materials such as polypropylene are able to withstand autoclaving processes better than piston nests formed from other polymeric materials. Alternatively, as radiation is another preferred method of sterilization, a material which is stable following exposure to standard radiation sterilization processes (e.g., gamma radiation), such as gamma stable polypropylene, is preferred. Other suitable materials will be apparent to those skilled in the art As shown particularly in FIG. 5, a single nesting unit 22 includes a generally hollow cylindrical body 28, also known as a chimney, which extends distally from (below) the web 24, to form an open lower end 29. The nesting unit 22 may also include one or more retention members 30, which are used to retain individual pistons 26 within cylindrical bodies 28 of the piston nest 10. In the current embodiment, the retention members 30 comprise diametrical protrusions that inwardly extend toward a central axis β of the cylindrical body 28 such that an individual piston 26 is retained within the cylindrical body 28 with a generally vertical orientation (parallel to the axis β). Further details on exemplary piston nest configurations are shown and described in U.S. Pat. No. 8,453,838. As such, the piston nest configuration shown and described herein should not be construed as limiting.

The purpose of the cover configurations and assembly and package embodiments, shown and described herein, is to protect interior portions of the pistons 26 and/or the hollow cylindrical bodies 28 of the piston nest 10 from a variety of potential contaminants. Such contaminants are of the type that would otherwise infiltrate the interior portions of the pistons 26 and the hollow cylindrical body 28. Contaminants may come from a variety of sources, including, but not limited to packaging materials and air particles.

The cover configurations shown and described herein are also used to provide at least some additional structural support to the piston nest 10. Preferably, each cover configuration provides at least some additional structural support that would assist in alleviating warping of piston nests 10 that is known to occur over time. Cover configurations may also be such that movement of the cylindrical bodies/chimneys 28 of the piston nest 10 is restricted. As such, the covers may have an interference fit with the piston nest 10 or pistons 26 included in a piston array.

FIG. 3 is a partially exploded perspective view of the cover 14 and the piston nest assembly 20, shown in FIG. 2. More particularly in FIG. 3, a first configuration of a cover 14 for the piston nest 10 is shown. The cover 14 is particularly suited for positioning over (but on the bottom of) the open lower ends 29 of the piston nest 10, as particularly shown in FIG. 5.

Referring to FIGS. 3, 4, 6, and 7, the cover 14 includes a plurality of cover sections 34 configured for positioning over a drug container piston array 12, preferably with the piston array 12 contained within a piston nest 10. FIG. 3 shows the cover 14 in alignment with the piston nest 10 and pistons 26 contained within respective nesting units 22 of the piston nest 10. Each individual cover section 34 includes an elongated cover body 36, having an open base or upper end 38, as particularly shown in FIGS. 3, 4, and 6, and a closed capped end bottom 40, as particularly shown in FIG. 7. Chamfers 41 (FIG. 4), 43a (inner chamfer, FIG. 4), 43b (outer chamfer, FIG. 7), may optionally be included around the base end 38 and/or the capped end 40 (interior portion 41, shown in FIG. 4). Chamfers 41, 43a, 43b are included around the base end 38 and/or the capped end 40 to facilitate insertion of the piston nest 14 into the cover 14. A wall 42 (FIG. 4) extends between the base end 38 and the capped end 40 such that the elongated cover body 36 is formed, as shown particularly in FIG. 7.

Figures 4, 5:
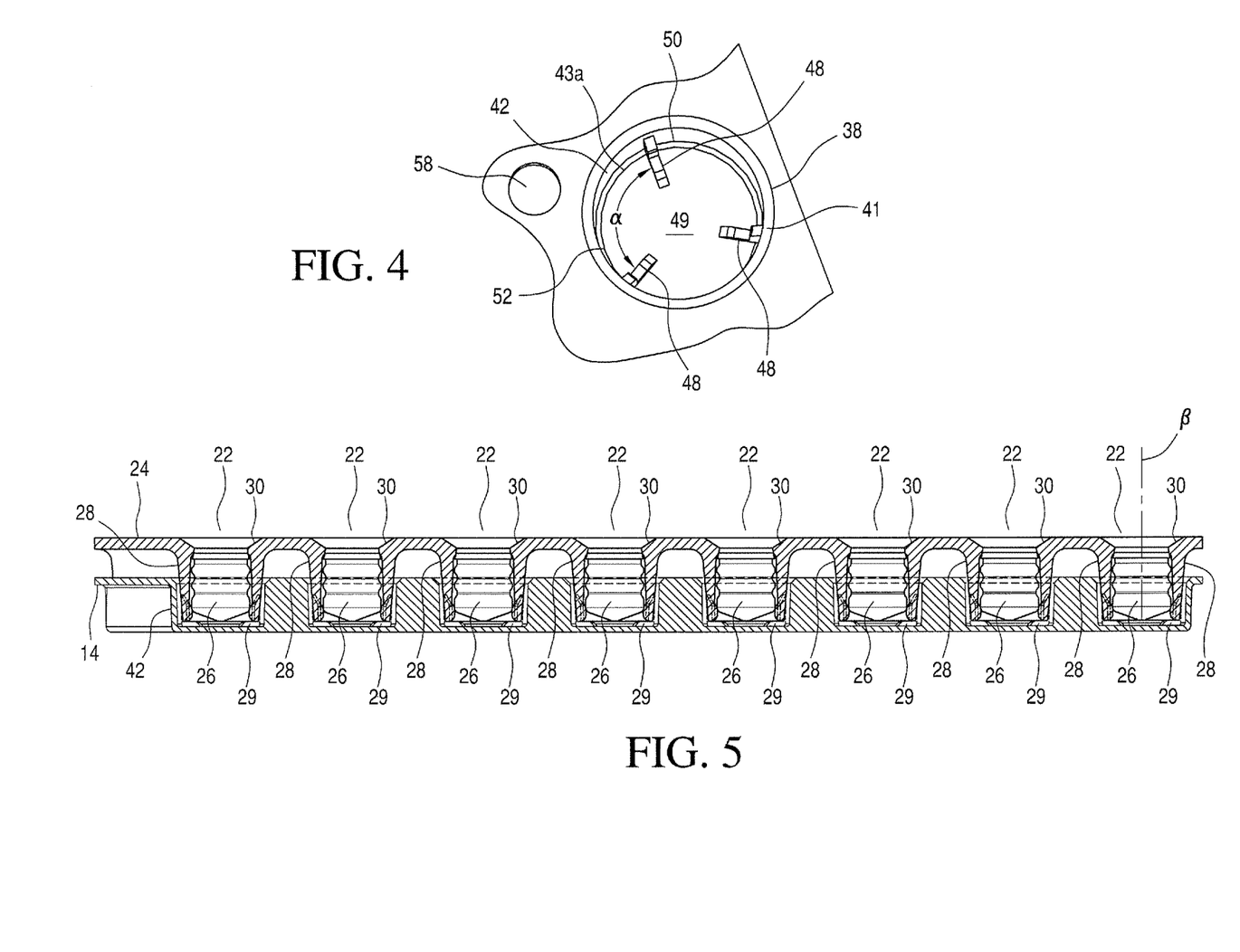
FIG. 4 is a greatly enlarged top plan view of the cover of FIG. 3, according to one preferred cover configuration.
FIG. 5 is an enlarged cross-sectional elevational view of the cover and piston nest assembly shown in FIG. 2, taken along line 5-5.

Positioned between each individual cover section 34 and coupled to each base end 38 is a plurality of base sections 46, as shown particularly in FIGS. 3 and 4. The base sections 46 are used to interconnect the cover sections 34. Upon formation of the cover 14, the cover sections 34 may be positioned to be laterally offset with respect to one another or configured in substantially aligned rows and columns, which are not offset with respect to one another. Cover section positioning, however, is preferably such that the cover 14 can be positioned over the open lower ends 29 of the cylindrical bodies 28 of various piston nest arrangements.

Figure 6:
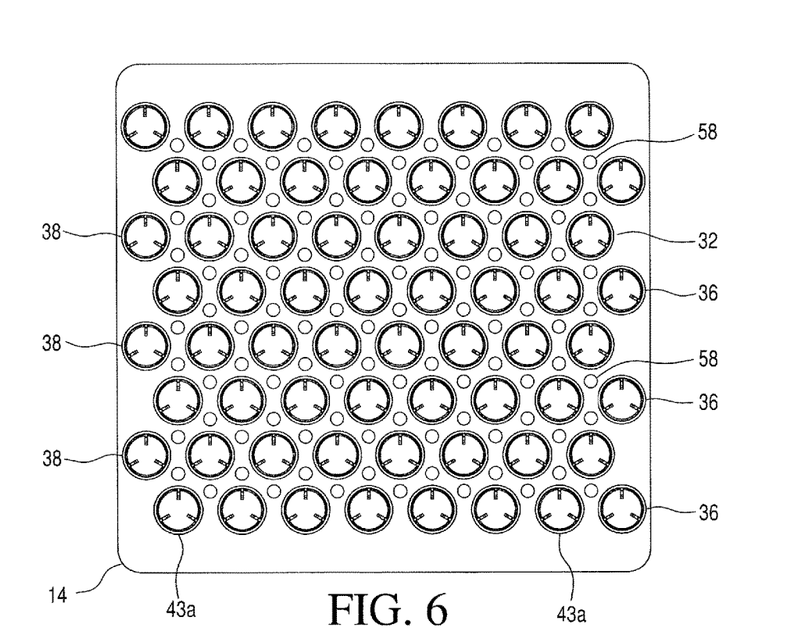
FIG. 6 is a top plan view of the cover for a drug container piston array shown in FIG. 3.

FIGS. 3 and 6, respectively show interior portions of the plurality of cover sections 34. Included within each cover section 34 is a plurality of locators 48, which are used to position and at least partially orient the cylindrical bodies 28 of the piston nest 10. Preferably, the locators 48 are positioned within each cover section 34 such that the orientation of the cylindrical bodies 28 is centered with respect to a central axis B. The locators 48 are preferably integrally incorporated into each cover section 34 and manufactured from materials that are the same as the cover 14. Preferably, the configuration of the locators 48 is such that each locator frictionally fits against and engages each cylindrical body 28 of each piston nest 10.

In the present cover configuration, three locators 48 are radially positioned on interior faces 49, 50 of the cover section body 44, as shown in FIG. 4. The locators 48 function to orient and locate the cylindrical bodies 28 of the piston nest 10. Preferably, each respective locator 48 is disposed on an inner edge 52 and positioned between the distal end of the wall 42 and the capped end 40 of the cylindrical body 28. The plurality of locators 48 are also radially positioned at substantially equidistant intervals around the inner diameter of the cover section body 44. FIG. 4 shows individual piston locators 48 positioned at an angle α, with respect to one another, which is approximately 120° (degrees). Fewer or more locators 48 may be positioned within the cover section body 44, depending upon various factors, including the piston diameters. Preferably, the outer shape or perimeter of the cover 14, however, is complementary in shape and size to the outer shape or perimeter of a piston nest 10.

Figure 7:
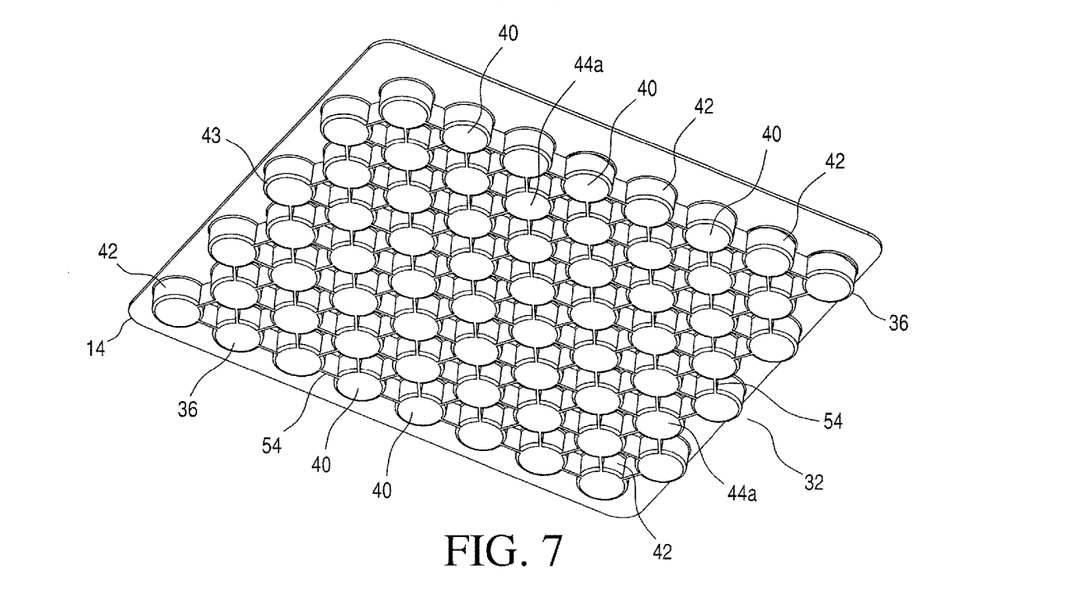
FIG. 7 is a bottom perspective view of the cover shown in FIG. 6.

FIG. 7 is a bottom perspective view of the cover 14, which includes a plurality of cover reinforcements 54 positioned between cover sections. Individual cover reinforcements 54 are preferably integral with individual cover sections 34 such that the cover 14 provides structural support of the piston nest 10 after insertion into the cover 14. Preferably, outer surfaces of the inner cover section bodies 44a have at least five cover reinforcements 54 positioned radially in substantially equidistant intervals around the outer diameter of each inner cover section body 44a. Outer surfaces of outer cover section bodies 44b have cover sections that inwardly extend toward the center of the cover 14 and at least one cover reinforcement 54 positioned on a side of the cover section body 44. The overall configuration of the cover 14 from a bottom perspective due to the positioning of the cover section bodies 44 and the cover reinforcements 54 results in a honeycomb-like configuration, as shown particularly in FIG. 7.

To facilitate the passage of sterilizing agents and/or process agents (e.g. steam from an autoclave) through the cover 14 and the piston nest 10, base sections 46 may include apertures 58, as shown in FIGS. 3, 4, and 6. Although shown with a circular shape, the aperture shape should not be limiting. As used herein, the term "aperture" should be broadly construed as any opening positioned in base sections 46, which is suitable for the passage of sterilizing agents and/or process agents. As such, the aperture 58 may have a slot, square, oval, or other polygonal shape.

The cover 14 may be attached to the piston nest assembly 20 with either an interference fit or a clearance fit, however a slight clearance fit is preferred. With an interference fit, the interior face 50 of the wall 42 of the cover 14 abuts against exterior surfaces of the cylindrical bodies 28 of the piston nest 10. The piston nest assembly 20 may alternatively be inserted into the cover 14 to have a clearance fit such that there is generally a small space between the interior face 50 of the wall 42 of the cover 14 and the exterior surfaces of the cylindrical bodies 28 of the piston nest 10. However, with either an interference fit or a clearance fit, the open lower end 29 of the cylindrical body 28 preferably rests against the locators 48 and the interior face 49 of the cover 14.

Figure 8:
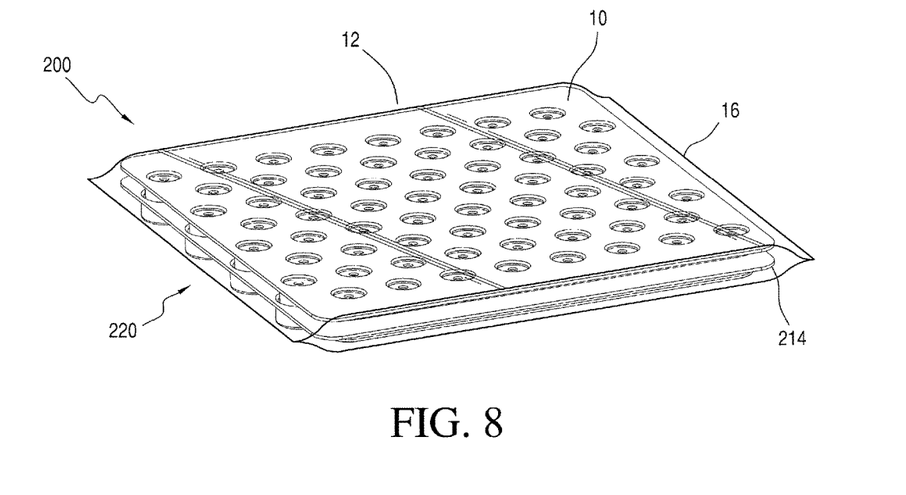
FIG. 8 is a perspective view of a package, including a second embodiment of a container and a cover and piston nest assembly in accordance with the present invention.
Figure 9:
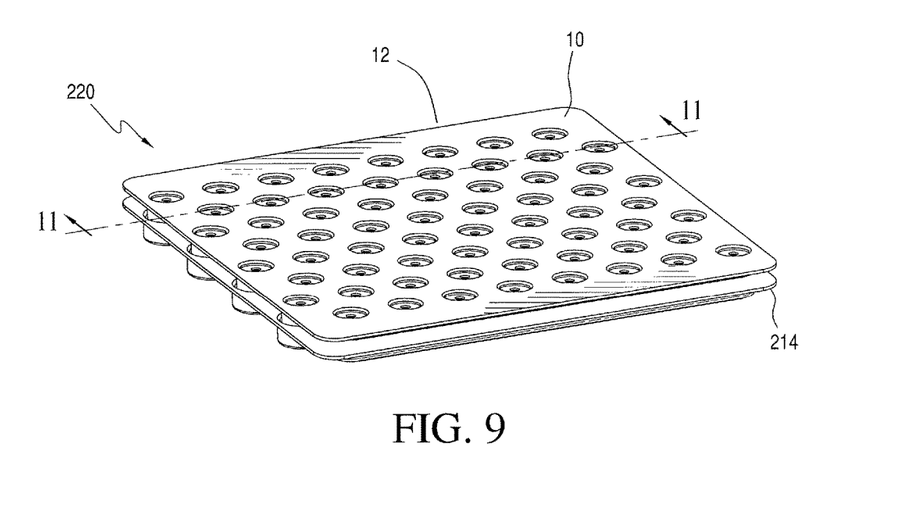
FIG. 9 is a perspective view of the cover and piston nest assembly included in the package of FIG. 8.

FIGS. 8 to 13 show a second embodiment of a cover 214 and a piston nest assembly 220. FIG. 8 shows a package 200 that includes the same piston nest 10, drug container piston array 12, and container 16, shown in FIG. 1. The cover 214, however, has a different configuration such that rows or columns of a piston array or cylindrical bodies of a piston nest are positioned in a plurality of transversely elongated cover sections 234. FIG. 10 is a partially exploded view of the cover and piston nest assembly 220, shown in FIG. 9.

The cover 214 includes a plurality of transversely elongated cover sections 234 configured for positioning over rows or columns a drug container piston array 12, preferably with the piston array contained within a piston nest 10. FIG. 10 shows the cover 214 in alignment with the piston nest 10 and pistons 26 contained within respective nesting units 22 of the piston nest. Each respective cover section 234 includes an open base or upper end 238 and a closed capped or lower end 240. Chamfers 241, 243 may also be optionally included around the outer perimeter of the base end 238 and/or the inner edge 252 of the capped end 240. Chamfers located on the inner edge 252 may also serve to facilitate distribution of sterilizing and processing agents along the cover sections.

Figure 11:
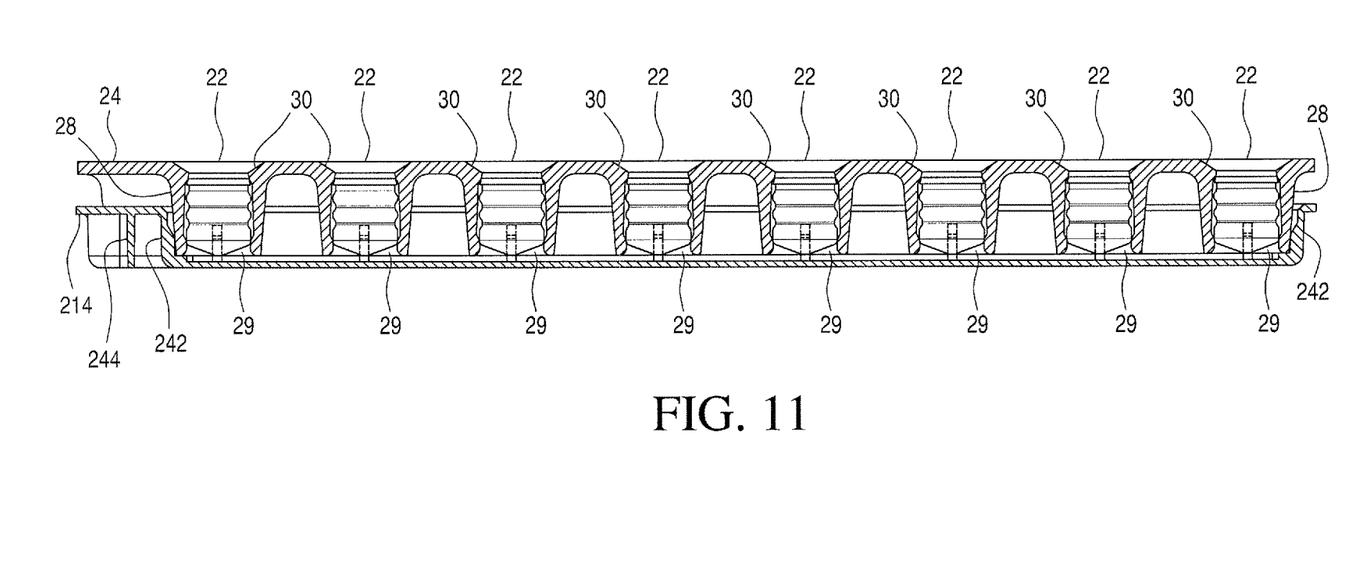
FIG. 11 is an enlarged cross-sectional elevational view of the cover and piston nest assembly shown in FIG. 9, taken along line 11-11.
Figure 13:
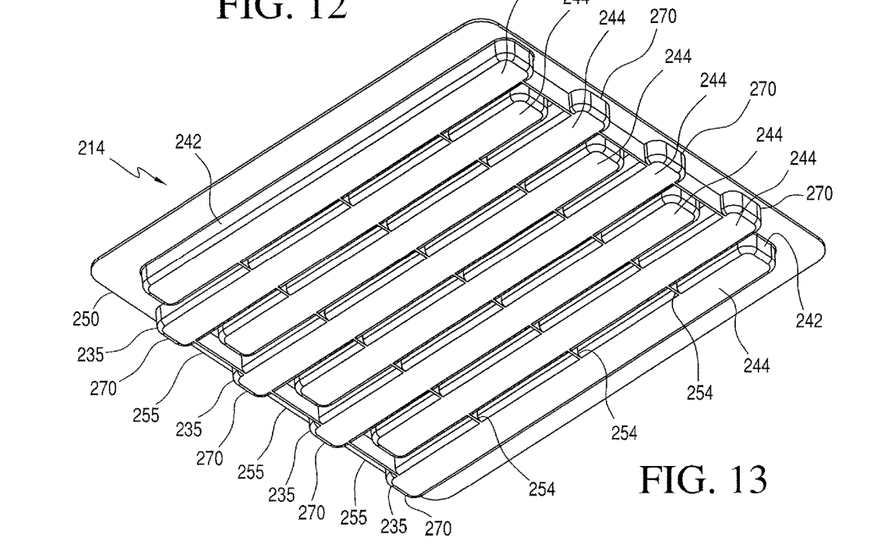
FIG. 13 is a bottom perspective view of the cover shown in FIG. 12.

A wall 242 extends between the base end 238 and the capped end 240 such that a cover section body 244 is formed, as shown particularly in FIGS. 11 and 13. Upon formation of the cover 214, cover sections 232 may be positioned to be laterally offset with respect to one another or in configured in rows, which are substantially aligned (i.e. not laterally offset).

Positioned between each cover section 234 and coupled to each base end 238 to extend around the cover is an interconnecting cover web 246. The interconnecting cover web 246 preferably has an outer perimeter 250 that is similar to that of the piston nest 10, as shown in FIG. 10.

Figure 12:
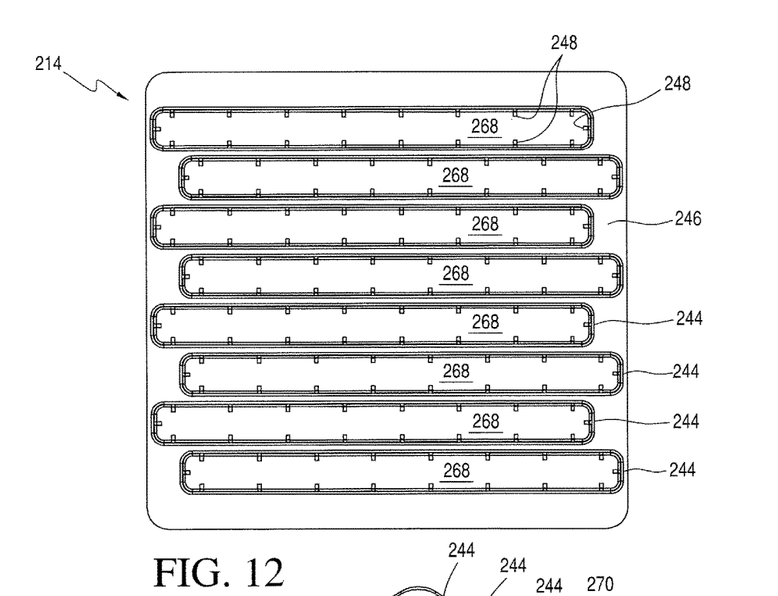
FIG. 12 is a top plan view of the cover for a drug container piston array shown in FIG. 10.

FIGS. 10 and 12, respectively show interior portions of the plurality of cover sections 234. Included within the interior of each cover section 234 is a plurality of locators 248, which are used to position and at least partially orient rows and/or columns of a piston array or a piston nest 10. In this configuration, the locators 248 are positioned at intervals along sidewalls 260, 262, 264, 266 and the bottom wall 268 of the cover section body 244.

FIG. 10 shows a total of 18 locators 248—one locator positioned on sidewalls 246, 266 and eight locators positioned on sidewalls 260, 262. The numbers of locators positioned within the cover section body 244, however, should not be construed as limiting. Fewer or more locators 248 may be positioned within the cover section body, depending, in part, on the total number of pistons 26 and/or cylindrical bodies 28 of the piston nest 10.

FIG. 13 is a bottom perspective view of the cover 214, and particularly shows a plurality of cover reinforcements 254 positioned between cover sections 234. Individual cover reinforcements 254 are preferably integral with individual cover sections 234 such that the cover 214 provides structural support of rows and/or columns of the piston nest 10 after insertion into the cover 214. Here, the cover reinforcements 254 are coupled to outer surfaces of the cover section bodies 244 and positioned at intervals transversely along the length of each cover section. The cover also include lateral cover reinforcements 255 coupled to end walls 235 and disposed between the outermost ends 270 of cover sections 234 (i.e. those closest to the outer perimeter 250).

Materials used in the manufacture of the cover configurations 14, 214 described herein are not necessarily limited to materials used to manufacture piston nests (e.g. rigid or semi-rigid polymeric materials). Cover materials are, however, preferably polymeric such that they formed by molding and other similar manufacturing methods. Preferred materials are also suitable for use with processes used to sterilize piston nests.

It will be appreciated by those skilled in the art that changes could be made to the embodiments and configurations disclosed herein without departing from the broad inventive concept thereof. It is to be understood, therefore, that the present invention is not limited to the particular embodiments and configurations disclosed. Rather, the present disclosure is intended to cover modifications within the spirit and scope of the appended claims.

The invention claimed is:

1. A cover for a drug container piston array or piston nest including a plurality of spaced apart single nesting units interconnected by a nest web and each having a cylindrical body extending distally from the nest web, each single nesting unit for retaining a piston therein, the cover comprising:
   a plurality of cover sections configured for positioning over the drug container piston array, each cover section comprising an elongated cover body having an open base end, a closed capped end, a wall extending between the base end and the capped end, and a plurality of piston locators positioned in spaced intervals along the wall of each elongated cover body, each piston locator being located on both the wall and an interior face of the capped end of each elongated cover body, the piston locators being configured and positioned to position and radially orient the cylindrical bodies of the piston nest within the corresponding elongated cover bodies; and
   a plurality of base sections positioned between the plurality of cover sections and coupled to each base end.

2. The cover of claim 1, wherein at least two of the plurality of cover sections are laterally offset with respect to one another.

3. The cover of claim 1, further comprising a plurality of cover reinforcements positioned between at least two of the plurality of cover sections.

4. The cover of claim 3, wherein at least one of the plurality of cover reinforcements is coupled to an outer wall surface of each of the plurality of cover sections.

5. The cover of claim 1, further comprising at least one cover reinforcement positioned between at least two of the plurality of cover sections and coupled to the base end of at least two cover sections.

6. The cover of claim 5, wherein the at least one cover reinforcement is coupled to an outer wall surface of at least one cover section.

7. The cover of claim 1, wherein the at least one cover reinforcement is integral with at least one cover section.

8. The cover of claim 1, wherein the plurality of piston locators are integrally incorporated into each cover section.

9. The cover of claim 1, wherein at least one of the open base end and the closed capped end of the elongated cover bodies includes a chamfer.

10. The cover of claim 1, further comprising at least one aperture disposed in at least one of the base sections to facilitate passage of at least one of a sterilizing agent and a process agent through the cover.

11. The cover of claim 1, wherein the piston locators are positioned within each cover section to orient the cylindrical bodies of the piston nest so that the cylindrical bodies of the piston nest are centered within the corresponding elongated cover bodies.

12. A packaging assembly for a drug container piston array, comprising:
   a package;
   a drug container piston array disposed within the package; and
   a cover disposed within the package and positioned over the drug container piston array disposed within the package, wherein the packaging assembly is configured to protect the array of pistons, and wherein the cover comprises:
      a plurality of cover sections configured for positioning over the drug container piston array, each cover section comprising an elongated cover body having an open base end, a closed capped end, a wall extending between the base end and the capped end, and a plurality of piston locators positioned in spaced intervals along the wall of each elongated cover body, each piston locator being located on both the wall and an interior face of the capped end of each elongated cover body, the piston locators being configured and positioned to axially and radially orient the cylindrical bodies of the piston nest within the corresponding elongated cover bodies; and
      a plurality of base sections positioned between the plurality of cover sections and coupled to each base end.

13. A method of covering a drug container piston array or piston nest, comprising:
   positioning a cover over the drug container piston array to prevent infiltration of at least some contaminants into an interior of at least some pistons included in the drug container piston array, wherein the cover comprises:
      a plurality of cover sections configured for positioning over the drug container piston array, each cover section comprising an elongated cover body having an open base end, a closed capped end, a wall extending between the base end and the capped end, and a plurality of piston locators positioned in spaced intervals along the wall of each elongated cover body, each piston locator being located on both the wall and an interior face of the capped end of each elongated cover body, the piston locators being configured and positioned to axially and radially orient the cylindrical bodies of the piston nest within the corresponding elongated cover bodies; and
      a plurality of base sections positioned between the plurality of cover sections and coupled to each base end.

14. The method of claim 13, further comprising disposing the cover and the drug container piston array or piston nest within a package.

* * * * *

UNITED STATES PATENT AND TRADEMARK OFFICE
CERTIFICATE OF CORRECTION

| | | |
|---|---|---|
| PATENT NO. | : 10,434,242 B2 | Page 1 of 1 |
| APPLICATION NO. | : 15/541182 | |
| DATED | : October 8, 2019 | |
| INVENTOR(S) | : James Thompson et al. | |

It is certified that error appears in the above-identified patent and that said Letters Patent is hereby corrected as shown below:

In the Claims

Column 7, Claim number 7, Line number 64, should read:
The cover of claim 5, wherein the at least one cover reinforcement is integral with at least one cover section.

Signed and Sealed this
Sixth Day of October, 2020

Andrei Iancu
*Director of the United States Patent and Trademark Office*